United States Patent

Plant Pat. 3,793

Patented Oct. 7, 1975

3,793

APPLE ROOTSTOCK

Henry M. Tydeman, East Malling, England, assignor to National Seed Development Organisation Limited Filed July 23, 1974, Ser. No. 490,956

Int. Cl. A01h *5/03*

U.S. Cl. Plt.—34 1 Claim

ABSTRACT OF THE DISCLOSURE

Apple rootstock of dwarfing type originated as a seedling by crossing pollen from the apple rootstock, Malling 9 (M. 9) onto flowers of the apple rootstock Malling 13 (M. 13). One seedling thereof was found to have exceptional dwarfing characterisics, which have continued through succeeding generations through asexual reproduction by stooling and by cuttings.

SUMMARY OF THE INVENTION

The original plant was a member of a family of seedlings, AK 1–29, produced by H. M. Tydeman by pollinating flowers of the apple rootstock Malling 13 (M. 13) with pollen from the apple rootstock Malling 9 (M. 9) in the spring of 1929. After trials to determine how easily members of the family AK 1–29 could be propagated vegetatively by the stooling method, a selection was made in 1934 of several including seedling number 3431. Subsequently, its vigor and precocity as a rootstock was assessed on the basis of nursery trials and anatomical characteristics as revealed in cross sections of the roots. These test indicated that number 3431 was an exceptionally dwarf rootstock and it was accordingly included in a replicated field trial, planted at East Malling Research Station, Maidstone, Kent, England, during the winter of 1946.

The present interest in intensive systems of apple growing is stressing the need for very dwarfing rootstocks, more dwarfing than the most dwarfing existing rootstock, M. 9. This apple rootstock is now designated as Malling 27 (M. 27).

A sexual reproduction of M. 27 by stooling and by cuttings has proved that its dwarf, precocious character is stable and is transmitted without change to the rootstocks propagated from it in these ways.

BRIEF DESCRIPTION OF DRAWINGS

The accompanying drawings show typical specimens of the improved apple rootstock, some in color as nearly true as it is reasonably possible to make the same in a color illustration of this character.

DETAILED DESCRIPTION

Figure 1:
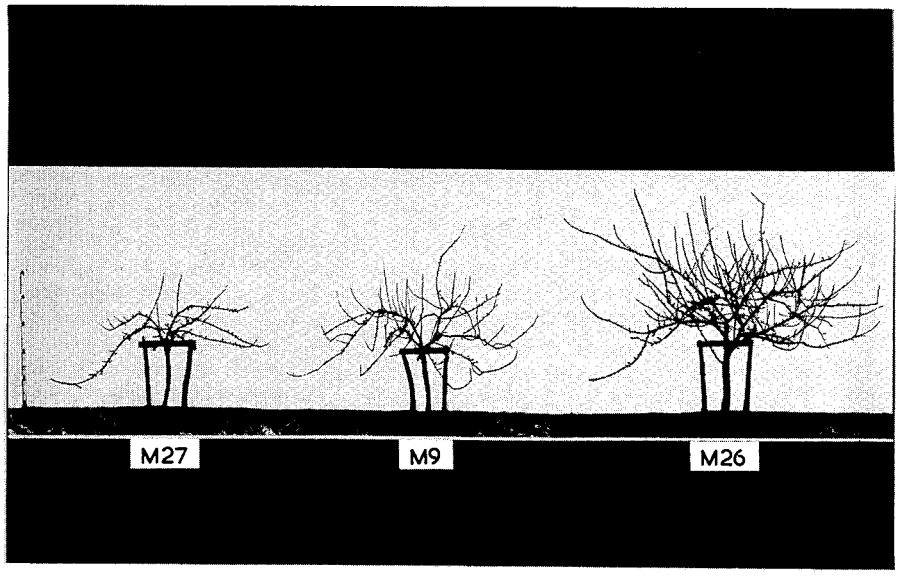
FIG. 1 is a view of the improved variety (M. 27) as a rootstock for Cox's Orange Pippin trees (8 years old) as compared with other dwarfing Malling rootstocks showing the effect of rootstock on tree size.
Figure 2:
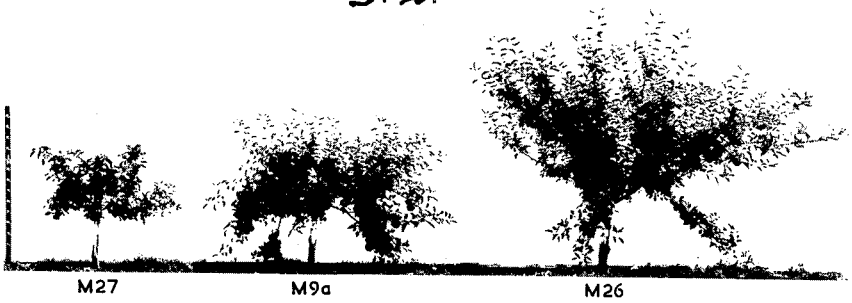
FIG. 2 shows fruiting trees of Cox's Orange Pippin (6 years old) on Malling 27, as compared with other dwarfing types.
Figure 3:
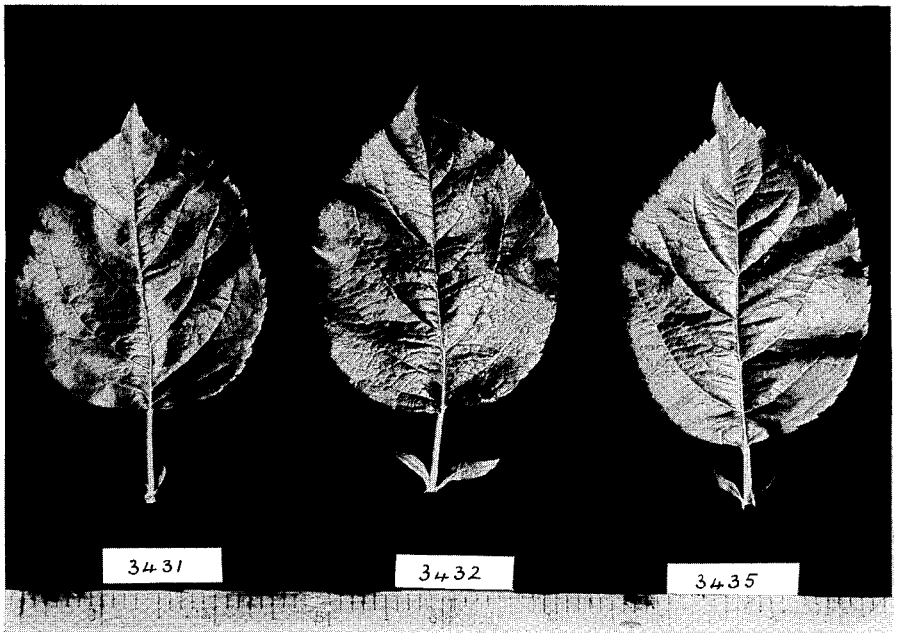
FIG. 3 is a view of a leaf of the new variety compared with two other Malling 9 derivatives.
Figure 4:
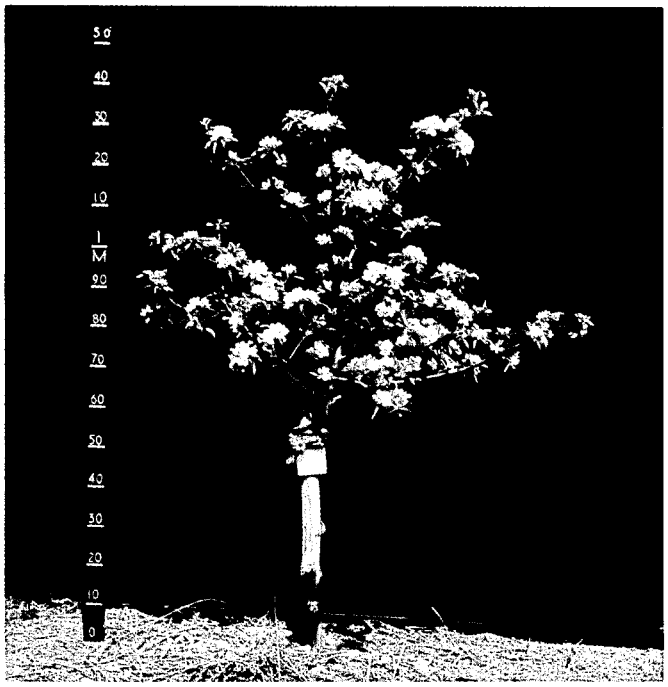
FIG. 4 is a view of Cox's Orange Pippin on the improved rootstock (M. 27) at 7 years of age.
Figure 5:
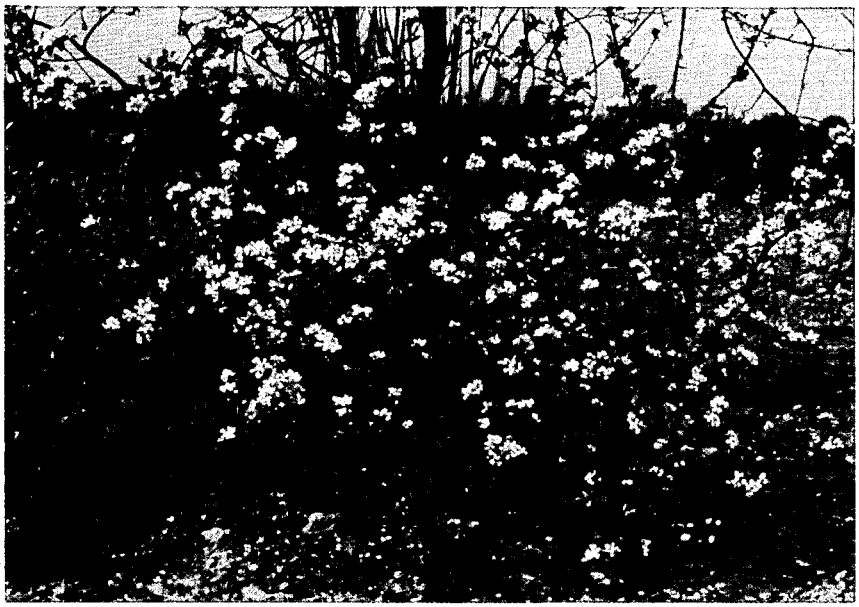
FIG. 5 is a view of a 12 year old tree of Malling 27, showing the prolific blooming, shrubby habit (approximately 1 meter high)
Figure 7:
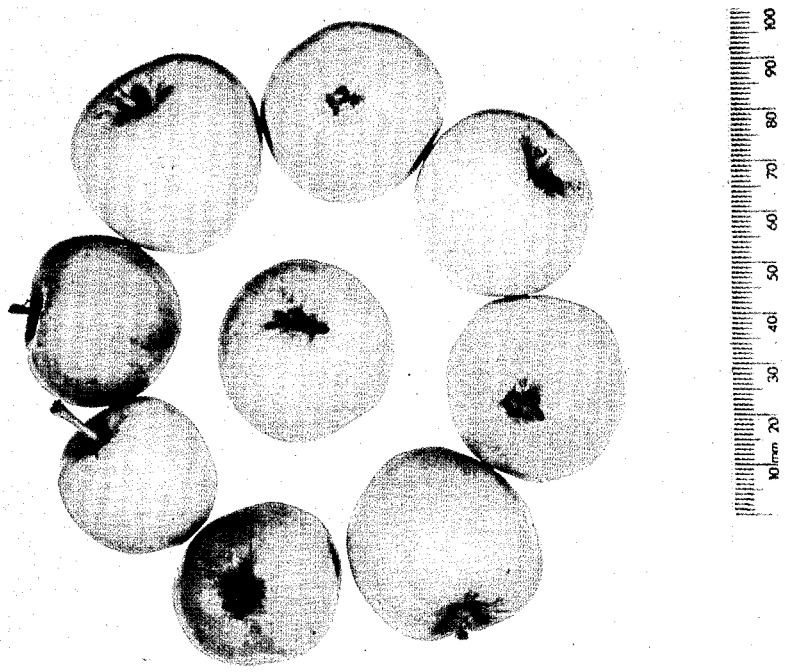
FIG. 7 is a view of the Malling 27 fruit showing size, shape and color.
Figure 6:
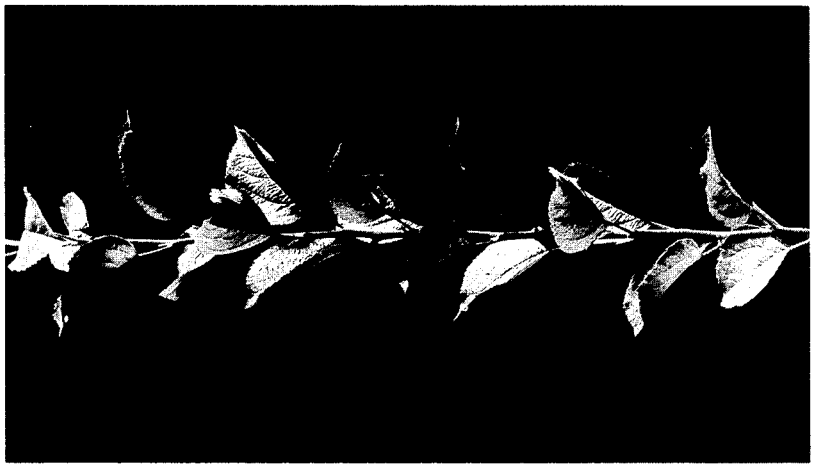
FIG. 6 is a view of a vegetative shoot of the improved variety, showing the deeply upfolded and upturned leaves with upturned petioles and small fairly serrate, crescent shaped stipules.

The following is a detailed description of the new rootstock. As a rootstock, the characteristics of the one year old shoots produced in the propagation nursery are those most often seen and used in identification. Blossom and fruit characters are included for completeness but are of little use because rootstocks are not normally grown on to form mature fruiting trees. Colors of leaves and shoots vary with growing conditions and are not considered of value in identifying the rootstock.

In a few cases where a precise assessment of color can be made reference is given to Munsell Color Charts for Plant Tissues, 1st Edition (1952), Munsell Color Co., Inc., Baltimore, Md., U.S.A. The color description given herein has reference to plants grown at the East Malling Research Station, Kent, England.

Asexual reproduction of the new variety (M. 27) by stooling and cuttings, as performed at the East Malling Research Station, Kent, England, shows that the described characteristics and distinctions come true to form and are transmitted through succeeding propagations.

FLOWER AND FRUIT CHARACTERS

Flowers: Medium flowering date in comparison with other apple rootstocks and scion varieties; medium size. Buds, pink, flowers mostly white when open.

*Date of bloom.*—May 2, 1969, May 8, 1970, May 4, 1971, April 26, 1972.

Fruit: No commercial value

*Harvest date.*—September 18, 1970, October 5, 1971, October 6, 1972.

Size: Small, variable. Axial diameter 3.1 cm. (2.73–3.34). Transverse diameter 3.5 cm. (3.00–381)

Shape: Irregular. Slopes at "eye" end. Angular in cross section.

Color: Yellowish green, becoming citrus yellow with pink flush over quarter to half of fruit surface when ripe.

Skin: Some russet around the stem and a little around the "eye." A few tiny flecks of russet elsewhere on the skin. Lenticels inconspicuous.

Calyx: Closed "eye."

Stem: Average length 1.07 cm. (0.53–1.21).

Flesh: Creamy-white turning brown quickly on exposure to air. Very dry, very chewy, very astringent flavor, pH 3.5. Sugar content 18%.

Core: Approximately one-eighth of fruit volume. Sometimes only four carpels produced, most of which contain one or more (up to three) fat seeds. One or more of the carpels per fruit are usually completely flat and contain no seeds.

Seed: Average dimensions 6.8 x 5.0 x 2.3 mm. About one-fifth of the seeds are flat. Less than five percent of the seeds are minute.

DESCRIPTION OF ONE YEAR VEGETATIVE SHOOTS FROM STOOLBED

Disinctive points

Weak, spreading shoots with smallish, deeply upfolded and upturned leaves; upturned petioles and small, faintly serrate, crescent shaped stipules. In winter the rather weak, deep chocolate brown (Munsell 2.5 YR 4/2) shoots have a distinctly longitudinally grained look with few, yellowish-brown (Munsell 7.5 YR 8/4) lenticels and small, pointed, greyish (Munsell 5. OY 8/2), slightly ragged, adpressed buds.

General habit:

*Strength of growth.*—Rather weak, spreading, thin flexible shoots.

*Habit of growth.*—Spreading.

*Number of laterals.*—Very few.

*Feathering.*—Little.
*Number of shoots on stools.*—Not very prolific.
Wood—summer:
*Color.*—Bright chocolate brown.
*Hairiness.*—Covered with a very thin whitish pubescence.
*Texture.*—Distinctly grained.
Wood—winter:
*Stoutness.*—Slender.
*Diameter of shoots.*—Between the buds 4.1 mm., across the buds 4.4 m., through the buds 5.0 mm.
*Flexibility.*—Flexible.
*Internodes.*—Short (24 mm.) slightly zigzagged.
*Color.*—Deep chocolate brown (Munsell 2.5YR 4/2).
*Hairiness.*—A little pale pubescence.
*Texture.*—Distinctly longitudinally grained and striated.
Lenticels:
*Number.*—Few (2 per cm. of shoot).
*Conspicuousness.*—Summer conspicuous, winter indistinct.
*Shape.*—Summer rather oval, winter rounded.
*Color.*—Yellow-brown (Munsell 7.5YR 8/4).
*Distribution.*—Scattered.
*Size.*—Smallish.
Leaves:
*Size.*—Smallish, length 53 mm., breadth 38 mm. length of leaf tip 5 mm.
*Shape.*—Medium oval.
*Base.*—Rounded.
*Apex.*—Abruptly acuminate slightly drawn out.
*Serrations.*—Acutely serrate (72 serrations).
*Surface.*—Deeply upfolded.
*Margin.*—Raised and waved.
*Pose in relation to stem.*—Much upturned.
*Color.*—Dull green.
*Hairiness on under surface.*—Fairly hairy.
*Texture.*—Smooth and crisp.
*Color of tips of shoots*—Pale green, slightly bronzed.
Leaf stalk:
*Shape.*—Slender, channelled.
*Length.*—Fairly long (16 mm.).
*Color.*—Deeply tinged wine red, extending up the lamina.
*Pose.*—Much upturned.
Stipules:
*Size.*—Small, length 5 mm., breadth 1 mm.
*Margin.*—Faintly serrate.

*Shape.*—Crescent shaped, shortly petiolate.
*Pose.*—Elect.
Season of leaf break: Early.
Time of defoliation: Very late.
Color of foilage in autumn: Medium green, leaf margins turned brown.
Buds:
*Size.*—Smallish, length 3.4 mm., breadth 3.3 mm.
*Shape.*—Broadly oval-triangular, with an acute apex.
*Compactness.*—Slightly ragged at the edges.
*Color.*—Greyish (Munsell 5.0Y 8/2) with patches of brownish-red (Munsell 7.5R 3/4).
*Hairiness.*—Some fine silvery hairs.
*Pose.*—Closely adpressed to shoot.
*Base.*—Little extended, slightly clawed.

GENERAL CHARACTERISTICS

Suckering: Rare.
Size control potential: Grafted varieties are significantly smaller than the same varieties on Malling 9.
Yield potential: Grafted varieties produce a higher proportion of fruit relative to wood than the same varieties on Malling 9 rootstocks.
Root bark ratio: For a root of a given size the bark of Malling 27 is thicker than the bark of an equivalent root of Malling 9.
Palisade cells per unit area of leaf: For a given set of environmental conditions Malling 27 has fewer palisade cells per unit area of leaf in July than equivalent leaves from the rootstocks Malling 2, Malling 4, Malling 12 and Malling 26.
Stomata per unit area of leaf: For a given set of environmental conditions, Malling 27 has fewer stomata per unit area of the lower surface of the leaf than equivalent leaves of the rootstocks, Malling 25, Malling Merton 106 and Malling Merton 111.
Induction of precocious fruiting in scion varieties: Scion varieties came into fruit production more quickly on Malling 27 than on Malling 7 or Malling 16.

I claim:

1. Apple rootstock of the dwarfing type, substantially as illustrated and described, produced as a seedling by pollinating flowers of the apple rootstock Malling 13 with pollen from the apple rootstock, Malling 9, and characterized as an exceptionally dwarf rootstock.

No references cited.

ROBERT E. BAGWILL, Primary Examiner